United States Patent
Hardy et al.

(10) Patent No.: US 11,919,975 B2
(45) Date of Patent: *Mar. 5, 2024

(54) PROCESS FOR PRODUCING LOW ENDOTOXIN CHITOSAN

(71) Applicant: MEDTRADE PRODUCTS LIMITED, Crewe (GB)

(72) Inventors: Craig Hardy, Cardigan (GB); Andrew Hoggarth, Crewe (GB); June Gladman, Warrington (GB)

(73) Assignee: MEDTRADE PRODUCTS LIMITED, Crewe (GB)

(*) Notice: Subject to any disclaimer, the term of this patent is extended or adjusted under 35 U.S.C. 154(b) by 53 days.

This patent is subject to a terminal disclaimer.

(21) Appl. No.: 14/894,465

(22) PCT Filed: May 29, 2014

(86) PCT No.: PCT/GB2014/051648
§ 371 (c)(1),
(2) Date: Nov. 27, 2015

(87) PCT Pub. No.: WO2014/191755
PCT Pub. Date: Dec. 4, 2014

(65) Prior Publication Data
US 2016/0108138 A1     Apr. 21, 2016

(30) Foreign Application Priority Data

May 29, 2013 (GB) .................................. 1309606

(51) Int. Cl.
| | | |
|---|---|---|
| *A61L 26/00* | (2006.01) | |
| *A61K 31/722* | (2006.01) | |
| *A61L 15/28* | (2006.01) | |
| *A61L 15/40* | (2006.01) | |
| *C08B 37/00* | (2006.01) | |
| *C08B 37/08* | (2006.01) | |

(52) U.S. Cl.
CPC ........ *C08B 37/0003* (2013.01); *A61K 31/722* (2013.01); *A61L 15/28* (2013.01); *A61L 15/40* (2013.01); *A61L 26/0023* (2013.01); *A61L 26/0061* (2013.01); *C08B 37/003* (2013.01); *A61L 2300/232* (2013.01); *A61L 2300/418* (2013.01); *A61L 2400/04* (2013.01)

(58) Field of Classification Search
CPC ..... C08L 5/08; C08B 37/003; C08B 37/0003; C08B 37/08; A61L 2300/418; A61L 2300/232; A61L 26/0023; A61K 8/736
USPC ............................................. 514/55; 536/20
See application file for complete search history.

(56) References Cited

U.S. PATENT DOCUMENTS

| | | | | |
|---|---|---|---|---|
| 4,195,175 A | * | 3/1980 | Peniston | C08B 37/003 536/20 |
| 4,946,870 A | * | 8/1990 | Partain, III | A61K 8/736 261/DIG. 88 |
| 2005/0080245 A1 | * | 4/2005 | Hung | C08B 37/003 536/20 |
| 2006/0293509 A1 | | 12/2006 | Hung et al. | |
| 2008/0248508 A1 | * | 10/2008 | Baker | C08B 37/0003 435/7.92 |

FOREIGN PATENT DOCUMENTS

| | | | | |
|---|---|---|---|---|
| EP | 1859816 | | 11/2007 | |
| EP | 1859816 A1 | * | 11/2007 | ............. A61L 15/28 |
| TW | 593342 | | 6/2004 | |
| WO | 2006134614 | | 12/2006 | |
| WO | WO2006/134614 A1 | * | 12/2006 | ............. C03B 37/08 |
| WO | WO 2006/134614 A1 | * | 12/2006 | ............. C03B 37/08 |
| WO | 2008063503 | | 5/2008 | |
| WO | WO 2008/063503 A2 | * | 5/2008 | ............. C08B 37/00 |
| WO | 2013140190 | | 9/2013 | |

OTHER PUBLICATIONS

International Search Report to corresponding international patent appl. No. PCT/GB2014/051648, dated Sep. 17, 2014, 3 pages.

* cited by examiner

*Primary Examiner* — Ganapathy Krishnan
(74) *Attorney, Agent, or Firm* — TAROLLI, SUNDHEIM, COVELL & TUMMINO L.L.P.

(57) ABSTRACT

The present invention relates to a process for producing a low endotoxin alkali chitosan, chitin, chitosan derivative or chitin derivative, and also to a process for producing low endotoxin neutral chitosan, chitosan salt and chitosan derivatives, and to the products of such processes. The process comprises contacting chitosan, chitin, chitosan derivative or chitin derivative with an alkali solution to form a mixture; leaving the mixture for a period of less than 1 hour and optionally drying the mixture. The low endotoxin alkali chitosan may be used in the manufacture of other useful chitosan based products.

20 Claims, 1 Drawing Sheet

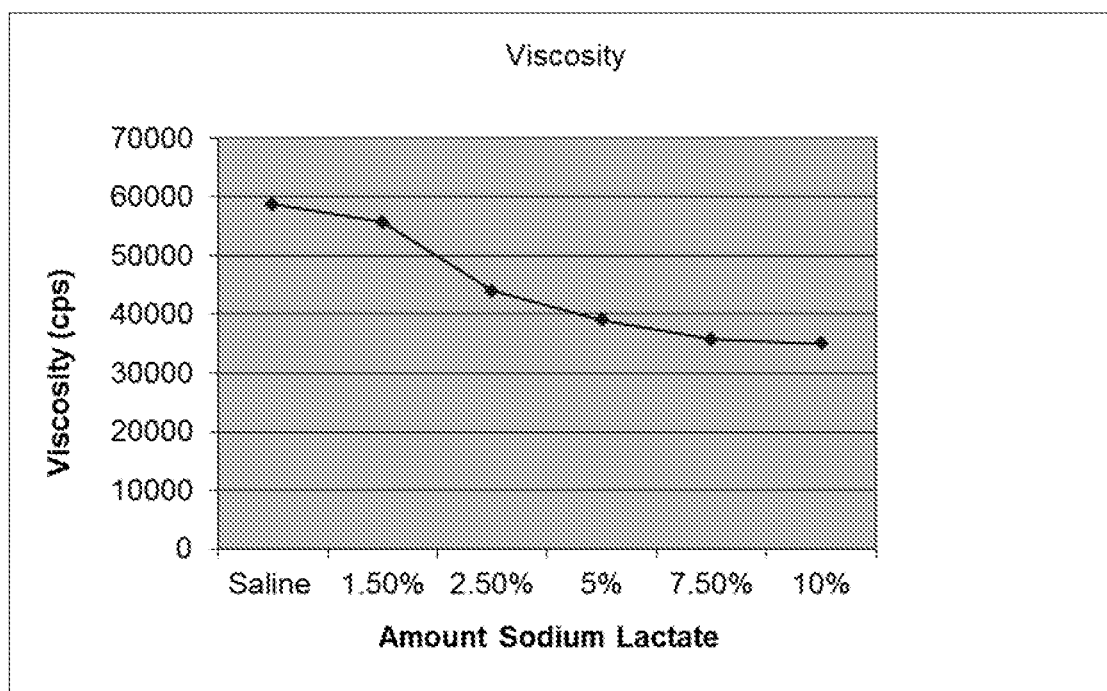

PROCESS FOR PRODUCING LOW ENDOTOXIN CHITOSAN

CROSS-REFERENCE TO RELATED APPLICATIONS

This application is the U.S. national phase entry of PCT/GB2014/051648, with an international filing date of May 29, 2014, which claims priority to and the benefit of GB 1309606.0, filed on May 29, 2013, the contents of which are hereby incorporated by reference in their entirety.

TECHNICAL FIELD

The present invention relates to a process for producing a low endotoxin alkali chitosan, and also to a process for producing low endotoxin neutral chitosan, chitosan salt and chitosan derivatives, and to the products of such processes.

BACKGROUND

Chitosan is particularly useful in the preparation of haemostatic materials for use in controlling bleeding.

Chitosan is a derivative of solid waste from shell fish processing and can be extracted from fungus culture. Chitosan is a water insoluble cationic polymeric material. Before using chitosan in haemostatic materials, it is often first converted into a water soluble salt. This way, the chitosan salt is soluble in blood to form a gel which stems blood flow.

Chitosan salts are ideally suited for the applications described herein as chitosan is readily broken down in the body. Chitosan is converted to glucosamine by the enzyme lysozyme and is therefore excreted from the body naturally. It is not necessary to remove chitosan from the body. Furthermore, chitosan salts exhibit mild antibacterial properties and as such their use reduces the risk of infection.

In order to utilise chitosan in the preparation of haemostatic materials that are suitable for use in controlling bleeding, it is necessary to ensure that the chitosan has a sufficiently low concentration of endotoxin.

Endotoxin is a lipopolysaccharide existing on the surface of the outer membrane of gram-negative bacteria. Endotoxins are highly toxic to mammals, particularly humans, and are notoriously difficult to remove from materials. Endotoxins may become pyrogenic when released into the bloodstream or other tissue where they are not usually found. Thus, endotoxin must be removed from pharmaceutically acceptable products.

Treatments to remove or destroy pyrogens, particularly endotoxin, are referred to as methods of 'depyrogenation'. Techniques for the depyrogenation of materials containing endotoxin include ion exchange chromatography, ultrafiltration, distillation and various chemical processes aimed at destroying endotoxin.

WO2008063503 relates to a method of removing endotoxin from chitosan including the following steps:
a) utilizing sterile pyrogen-free equipment and materials in a sterile environment;
b) swelling chitosan containing endotoxins for up to 24 hours;
c) dissolving 1 kg/25 L to 1.5 kg/25 L of the chitosan in 0.01M to 4.0M of a hydroxide base;
d) continuously stirring the resulting chitosan base solution;
e) heating the solution between 60-100° C. for 45 minutes to 4 hours with stirring;
f) rinsing the solution with up to 10× volume of ultra-pure endotoxin-free water;
g) neutralizing the solution to a pH between 6.8 and 7.5;
h) forming an ultra-pure low endotoxin chitosan slurry and transferring to a endotoxin-free closed system;
i) removing excess water from the slurry.

This is a complicated and costly process, especially with the need for sterile equipment and the need to rinse the solution with 10× volume of endotoxin-free water.

US2006293509 relates to a method of making a water soluble chitosan having low endotoxin by:
(a) contacting water-insoluble chitosan with a basic solution for a first period of time of greater than 1 hour;
(b) rinsing the water-insoluble chitosan to remove residual basic solution, desirably with endotoxin-free water;
(c) partially acetylating the water-insoluble chitosan in a reaction solution containing a phase transfer agent;
(d) dissolving the partially acetylated water-soluble chitosan in an aqueous solution containing a surfactant and having a pH of from about 7.0 at about 7.4;
(e) adding a water-miscible solvent into the aqueous solution and further adjusting the pH of the aqueous solution to a pH of at least 8.0 to cause precipitation of water-soluble chitosan having low endotoxin content from the aqueous solution/water-miscible solvent mixture; and
(f) optionally washing in a non-solvent such as isopropanol.

However, this process is complicated and expensive and desirably involves using large quantities of endotoxin-free water or other liquids. The process also requires the use of phase transfer agents and takes place over a few hours.

TW593342 relates to a method of reducing endotoxin in chitosan by:
(a) dissolving chitosan containing endotoxin in an aqueous solution;
(b) contacting the aqueous solution with a surfactant to form an insoluble solid and an aqueous solution reduced in the content of the endotoxin;
(c) using a solid/liquid separation means to separate the solid from the aqueous solution.

However, this process requires a surfactant to react with the dissolved chitosan to make an insoluble solid. The resulting solid will be a mixture of chitosan and surfactant or a reaction product between the chitosan and surfactant.

SUMMARY

The present invention aims to alleviate the aforementioned difficulties.

According to a first aspect of the present invention, there is provided a process for producing a low endotoxin alkali chitosan, chitin or a derivative thereof, the process comprising the steps of:
(a) contacting chitosan, chitin, a chitosan derivative or a chitin derivative with an alkali solution to form a mixture; and
(b) leaving the mixture for a period of less than 1 hour.

The process of the present invention may further comprise the step (c) of drying the mixture.

The process of the present invention provides an effective way of obtaining an alkali chitosan, chitin, chitosan derivative or chitin derivative having a low endotoxin concentration. Advantageously, the process does not require a washing step, a rinsing step, use of a surfactant or phase transfer agents, sterile equipment and/or the use of endotoxin free water. Further, specialist air filtration or sterile conditions are also not required. The process of the present invention preferably does not comprise a step of acetylating the chitosan. Further, the process of the present invention does not use endotoxin free equipment. This is particularly beneficial as it reduces the cost of the process compared to processes requiring such equipment.

By the term 'chitosan derivative' it is meant herein a partially deacetylated chitin, which may have different percentages of deacetylation, as desired. Typically, the partially deacetylated chitin suitable for use in the present invention has a deacetylation degree above about 50%, more typically above about 75% and most typically 5 above about 85%.

Also herein included within the term 'derivatives' are reaction products of chitosan or chitin with other compounds. Such reaction products include, but are not limited to, carboxymethyl chitosan, hydroxyl butyl chitin, N-acyl chitosan, O-acyl chitosan, N-alkyl chitosan, O-alkyl chitosan, N-alkylidene chitosan, O-sulfonyl chitosan, sulfated chitosan, phosphorylated chitosan, nitrated chitosan, alkalichitin, alkalichitosan, or metal chelates with chitosan, etc.

Whilst the first aspect of the present invention provides a process for producing low endotoxin chitosan, chitin or a derivative thereof, it is described hereinafter in relation to chitosan for convenience and illustrative purposes only.

The chitosan may be commercially available chitosan, such as food grade, medical grade or pharmaceutical grade chitosan. The process of the present invention may therefore be operable to provide low endotoxin alkali chitosan from commercially available chitosan. This is different to certain processes where endotoxins may be removed or reduced as part of a chitosan production process. Beneficially, the process of the present invention can be used to provide low endotoxin alkali chitosan from prepared chitosan that would otherwise have been unsuitable to the medical field due to its endotoxin concentration.

The term alkali chitosan is used herein to refer to a chitosan composition having a pH value of greater than pH 7.5.

The term alkali solution is used herein to refer to a solution having a pH value of greater than pH 7.5.

Since the molecular weight of endotoxins can vary significantly, endotoxin concentration is measured in endotoxin units (EU) per gram of material. The measurement of endotoxin concentration is a quantification of endotoxin levels relative to a specific quantity of reference endotoxin.

For example, in the present invention, the concentration of endotoxin is measured in endotoxin units (EU) per gram of chitosan. The term 'low endotoxin' is used herein to refer to an endotoxin concentration of less than 50 endotoxin units (EU) per gram of chitosan.

The process of the present invention is thus suitable for making an alkali chitosan that has an endotoxin concentration of less than 50 EU/g.

Preferably, the resulting alkali chitosan has an endotoxin concentration of less than 30 EU/g, more preferably less than 20 EU/g, more preferably less than 15 EU/g, even more preferably less than 10 EU/g and most preferably less than 5 EU/g.

It has been found that low concentrations of alkali solution are preferable in the present process. The concentration of alkali solution used in the process may be from around 0.01M to around 1M. Preferably, the concentration of alkali solution is less than 1M. More preferably, the concentration of alkali solution is from around 0.02M to 0.25M and even more preferably the concentration of alkali solution is around 0.04M to 0.06M, typically 0.05M. Concentrations of alkali solution can be up to around 0.01M, 0.05M, 0.10M, 0.15M, 0.20M, 0.25M, 0.30M, 0.35M, 0.40M, 0.45M, 0.50M, 0.55M, 0.60M, 0.65M, 0.70M, 0.75M, 0.80M, 0.85M, 0.90M or 0.95M. Good results have been observed with a concentration of 0.1M alkali solution.

In some embodiments, the quantity of alkali solution to chitosan may be in the range of from about 1 part chitosan to about 10 parts alkali solution up to about 10 parts chitosan to about 1 part alkali solution. Preferably, the quantity of alkali solution to chitosan is about 1 part alkali solution to about 2 parts chitosan, more preferably about 1 part alkali solution to about 1 part chitosan.

The alkali solution may comprise an alkali or alkaline earth component selected from the following, either alone or in combination: metal hydroxides, metal carbonates, metal bisulphites, metal persilicates, conjugate bases and ammonium hydroxide.

Suitable metals include sodium, potassium, calcium, or magnesium.

Preferably, the alkali component is sodium hydroxide, potassium hydroxide or sodium carbonate. Typically, sodium hydroxide is used.

The alkali solution may be contacted with the chitosan by any suitable means known in the art. For example, the alkali solution may be sprayed onto the chitosan or the chitosan may be mixed with the alkali solution. Preferably, there is an even distribution of alkali contacted chitosan.

Preferably, the chitosan is mixed with the alkali solution. At low molecular weights, the chitosan may completely or partially dissolve in the alkali solution. The chitosan may be mixed with the alkali solution in step (a) for up to around 30 minutes, more preferably for around 10 minutes. In some embodiments, the chitosan may be mixed with the alkali solution for greater than 30 minutes.

In some embodiments, the chitosan does not dissolve in the alkali solution.

In some embodiments, the chitosan does not swell in the alkali solution.

In some embodiments, the alkali solution wets the chitosan without dissolving or swelling the chitosan.

In some embodiments, the mixture of chitosan and alkali solution may be stirred intermittently for the duration of step (b).

The mixture of chitosan and alkali solution is left for a period of time in which sufficient endotoxin is destroyed. The mixture of chitosan and alkali solution is left for a period of less than one hour. It has been discovered that leaving the chitosan and alkali for a short period of time of less than one hour before subsequent processing results in a desirably low endotoxin concentration in the resulting alkali chitosan.

Suitably low concentrations of endotoxin have been observed when the mixture has been left for less than one hour. From a processing perspective, the less time the chitosan and alkali mixture is left the better. It is an advantage of the process of the present invention that the mixture can be left without the need for continued mixing of the chitosan with the alkali solution.

In some embodiments, the mixture may be left for a period of less than 60, 55, 50, 45, 40, 35, 30, 25, 20, 15, 10, or 5 minutes.

Preferably, the mixture is left for a period of less than three minutes, more preferably less than two minutes and most preferably less than one minute.

Preferably, the mixture is left in step (b) only for the period of time taken to prepare the mixture for a subsequent stage of processing, for example, the drying step (c). It has been observed that if you dry the mixture within one hour the endotoxin concentration lowers over time (around 1 to 3 weeks).

Good results have been observed when the mixture has been dried immediately following contacting chitosan with an alkali solution in step (a). In this context, immediately means that the mixture is only left in step (b) for the period of time it takes to prepare the mixture for the drying step (c). Typically, this is less than about 30 seconds, preferably less than 20 seconds and most preferably less than 10 seconds.

Thus, according to an aspect of the present invention there is provided a process for producing a low endotoxin alkali chitosan, chitin or a derivative thereof, the process comprising the steps of:
  (a) contacting chitosan, chitin, a chitosan derivative or a chitin derivative with an alkali solution to form a mixture; and
  (b) immediately drying the mixture.

In such a process, the mixture is left in step (b) for the time it takes to prepare it for the next stage of processing. For example, the mixture may be left in step (b) for the time it takes to prepare it for drying. The mixture may then be dried in a drying step (c).

The mixture may be left to stand in step (b) at room temperature and pressure. By room temperature and pressure, it is meant a temperature of around 20-25° C. and a pressure of about 1 atmosphere (atm). Beneficially, the mixture does not need to be left in a sterile environment.

The mixture is preferably stored in a clean container. The mixture may be stored under an inert atmosphere.

The mixture may further comprise a preservative. Beneficially, the preservative may eliminate the risk of microbial growth that may develop, for example, when the mixture is left for a prolonged period. The preservative may be any preservative that is biocompatible and suitable for use in an alkali environment. Suitable preservatives include silver ions, zinc ions, chlorohexadine, or combinations thereof.

The drying step may be performed by any conventional drying means known in the art. Preferably, the drying step is performed in an oven or by filtration through an air dryer. Again, specialist sterile equipment is not required for the drying step.

It has been discovered that, once the mixture has been dried in the drying step, the endotoxin level of the dry mixture does not noticeably increase over time. In fact, as noted above, it has been observed that the endotoxin level can lower over time. This is beneficial in that the mixture can be stored for a period of time prior to further processing.

There is thus provided a low endotoxin alkali chitosan having an endotoxin concentration of less than 50 EU/g. The low endotoxin alkali chitosan may be water insoluble. At low molecular weights, the low endotoxin alkali chitosan may show some water solubility.

According to a further aspect of the present invention, there is provided a low endotoxin alkali chitosan, chitin or a derivative thereof obtainable by the process as described herein.

According to a further aspect of the present invention, there is provided an alkali chitosan, chitin or a derivative thereof comprising an endotoxin concentration of less than 50 EU/g.

The alkali chitosan, chitin or a derivative thereof preferably has an endotoxin concentration of less than 30 EU/g, preferably less than 20 EU/g, more preferably less than 15 EU/g, even more preferably less than 10 EU/g and most preferably less than 5 EU/g.

The low endotoxin alkali chitosan, chitin or a derivative thereof may comprise alkali having a concentration of around 1M or less. Preferably, the concentration is from around 0.5M or less, more preferably from around 0.25M or less and even more preferably from around 0.2M or less and most preferably from around 0.1M or less.

The low endotoxin alkali chitosan may be used as an intermediate in the manufacture of other chitosan products, such as for example, derivatives or copolymers or in the manufacture of low molecular weight chitosan or chitosan oligosaccharides. The low endotoxin alkali chitosan may also be useful as a raw material for the manufacture of other forms of chitosan or derivatives or copolymers, such as chitosan based fibres, fabrics, coatings, films, gels, solutions, sheets or foams.

In particular, the low endotoxin alkali chitosan may be used in the preparation of other useful chitosan products having low concentrations of endotoxin, including neutral chitosan and chitosan salts and other chitosan derivatives, for example, carboxymethyl chitosan, hydroxyethyl chitosan, acyl chitosan, alkyl chitosan, sulphonyl chitosan, phosphorylated chitosan, alkylidene chitosan, metal chelates, chitosan chloride, chitosan lactate, chitosan acetate, chitosan malate, chitosan gluconate.

Thus, according to a further aspect of the present invention there is provided a process for producing a low endotoxin neutral chitosan, chitosan salt or chitosan derivative comprising the step of contacting an alkali chitosan prepared by the process described hereinbefore with an acid.

The process can provide medically useful neutral chitosan, chitosan salt or other chitosan derivative having low concentrations of endotoxin.

The step of contacting the alkali chitosan with the acid may be performed before the drying step (c) described hereinabove in the process for producing a low endotoxin alkali chitosan.

Alternatively, the step of contacting the alkali chitosan with an acid may be performed after the drying step (c) described hereinabove in the process for producing a low endotoxin alkali chitosan. In such embodiments, the process for producing a low endotoxin neutral chitosan, chitosan salt or chitosan derivative may comprise a further drying step after the step of contacting the alkali chitosan with an acid. The drying step may be performed by any conventional drying means known in the art. Preferably, the drying step is performed in an oven or by filtration of the product through an air dryer.

The acid may be contacted with the alkali chitosan by any suitable means known in the art. For example, the acid may be sprayed onto the alkali chitosan or the alkali chitosan may be mixed with the acid.

Preferably, the alkali chitosan is mixed with the acid.

A neutral chitosan is referred to herein to mean a chitosan composition having a pH value of between about pH 6.5 and about pH 7.5, and preferably about pH 7.

Thus, in order to prepare a neutral chitosan, the alkali chitosan may be mixed with an appropriate volume and/or concentration of acid to form a neutral solution having a pH of between 6.5 and 7.5. The volume and/or concentration of acid required to neutralise the alkali chitosan will be dependent on the pH of the alkali chitosan.

Alternatively, in order to prepare a chitosan salt or chitosan derivative, the alkali chitosan may be mixed with a volume and/or concentration of acid in excess of that required to provide a neutral chitosan.

A suitable acid for use in the present invention may be selected from the following, either alone or in combination:

organic acids, carboxylic acids, fatty acids, amino acids, lewis acids, monoprotic acids, diprotic acids, polyprotic acids, nucleic acids and mineral acids.

Suitable organic acids may be selected from the following, either alone or in combination: acetic acid, tartaric acid, citric acid, ascorbic acid, acetylsalicylic acid, gluconic acid and lactic acid.

Suitable fatty acids may be selected from the following, either alone or in combination: myristoleic acid, palmitoleic acid, sapienic acid, oleic acid, elaidic acid, vaccenic acid, linoleic acid, linoelaidic acid, α-Linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid.

Suitable amino acids may be selected from the following, either alone or in combination: histidine, lysine, aspartic acid, glutamic acid, glutamine, glycine, proline, taurine.

Suitable mineral acids may be selected from the following, either alone or in combination: hydrochloric acid, sulphuric acid and nitric acid. Preferably, the acid selected for the neutralisation is hydrochloric acid.

The acid may have a concentration of from about 0.001M acid up to the maximum possible concentration of acid. For example, the typical maximum concentration for sulphuric acid is around 98% sulphuric acid. The acid may have a concentration of from about 0.01M to 5M, 0.01M to 3M or 0.1M to 2M. Preferably, the acid has a concentration of about 1M. The concentration of acid may be up to about 0.01M, 0.05M, 0.10M, 0.15M, 0.20M, 0.25M, 0.30M, 0.35M, 0.40M, 0.45M, 0.50M, 0.55M, 0.60M, 0.65M, 0.70M, 0.75M, 0.80M, 0.85M, 0.90M, 0.95M or 1.0M.

The acid may be present as an acid liquor comprising the acid and a non-solvent. The non-solvent may be any solvent in which chitosan is insoluble. Typical non-solvents include ethyl lactate, ethyl acetate, methyl acetate, ethanol, acetone or mixtures thereof. Preferably, the non-solvent comprises ethyl acetate or ethanol. More preferably, the non-solvent comprises 80:20 ethanol in water. Beneficially, it has been observed that the reaction proceeds at a faster rate using a non-solvent comprising an 80:20 mixture of ethanol to water.

The ratio of chitosan to acid liquor may be from about 5 to 1 to about 1 to 5. Preferably, the ratio of chitosan to acid liquor is about 2 to 1.

In some embodiments, the low endoxotin alkali chitosan may be mixed with the acid for up to around 30 minutes or less, more preferably for around 10 minutes or less and most preferably for around five minutes or less. The reaction may then be allowed to happen as the mixture is dried.

The product resulting from the mixture of alkali chitosan with acid may contain an acid salt. Preferably, the alkali solution and acid are selected to ensure that the acid salt formed is biocompatible. For example, the alkali solution may comprise sodium hydroxide and the acid may comprise hydrochloric acid. In such an example, the acid salt would be the biocompatible salt sodium chloride.

The acid salt is formed as a by-product of the reaction between the alkali chitosan and the acid.

It has been discovered that the presence of an acid salt in the product can affect the usefulness of the resulting chitosan product. For example, it has been observed that chitosan gels to a lesser extent in saline solution than it does in water, and to an even lesser extent in saline solution at double concentration. Double concentrated saline solution referred to herein is contemplated as having an amount of sodium chloride of 1.8%. Consequently, it is desirable to have as low an amount of acid salt in the resulting chitosan product as possible and, ideally, a level of acid salt which makes little or substantially no difference to the effectiveness of the chitosan product.

It has surprisingly been discovered that using an alkali solution having a low concentration, such as less than 0.25M, preferably from 0.01M to 0.2M and more preferably from around 0.01M to around 0.1M, produces the desired low endotoxin concentration whilst also resulting in less acid salt by-product being produced in the subsequent process to produce a neutral chitosan, chitosan salt or chitosan derivative. Beneficially, less acid salt by-product has been found to result in a chitosan product that has improved gelling in use over products containing a higher amount of acid salt. The process of the present invention can provide a chitosan product with a suitably low amount of acid salt without the need to wash or rinse the chitosan product. This also has the added advantage of not requiring the use of endotoxin-free water in a washing or rinsing step.

It has also been found that using low concentrations of alkali solution as described herein causes less of a reduction in the viscosity of the chitosan when producing a neutral chitosan, chitosan salt or chitosan derivative.

By low concentrations of alkali, it is meant from around 0.01M to around 1M, preferably less than 1M, more preferably from around 0.02M to around 0.25M. In some embodiments, the alkali concentration may from 0.02M to 0.1M, preferably 0.05M to 0.1M. Good results have been observed using an alkali concentration of around 0.1M. In some embodiments, the alkali concentration may be as mentioned hereinabove. Beneficially, therefore, using low concentrations of alkali solution in the process is less damaging to the chitosan. It is therefore possible to remove endotoxin from chitosan whilst causing only minimal change in viscosity. It is desirable for the viscosity of the chitosan to reduce by less than about 25% in the process, preferably by less than about 15% and more preferably by less than about 10%.

Where the process provides a low endotoxin neutral chitosan, the product is suitable for use as an intermediate in the production of other chitosan based products. One particular use is in the production of chitosan salts, whose absorbent properties make them desirable for use in haemostatic preparations for controlling bleeding. It is preferable that the chitosan salts are water soluble.

Thus, in another embodiment of the present invention, a low endotoxin chitosan salt may be prepared by contacting a low endotoxin neutral chitosan produced by the process described herein with an acid.

The acid may be any acid appropriate for providing the desired chitosan salt. For example, if chitosan acetate is desired, acetic acid may be used; if chitosan succinate is desired, succinic acid may be used, etc. Any of the acids described herein may be used in the present process for producing a low endotoxin chitosan salt.

The process for producing a low endotoxin chitosan salt or chitosan derivative may further comprise the step of drying the mixture of low endotoxin neutral chitosan and acid. The drying step may be performed by any conventional drying means known in the art. Preferably, the drying step is performed in an oven or by filtration of the product through an air dryer.

There is thus provided a low endotoxin neutral chitosan, chitosan salt or chitosan derivative having an endotoxin concentration of less than 50 EU/g.

The low endotoxin neutral chitosan may be water insoluble.

The low endotoxin chitosan salt may be water soluble.

According to a further aspect of the present invention, there is provided a low endotoxin neutral chitosan, chitosan salt or chitosan derivative obtainable by any of the processes described herein.

According to a further aspect of the present invention, there is provided a neutral chitosan, chitosan salt or chitosan derivative comprising an endotoxin concentration of less than 50 EU/g.

The neutral chitosan, chitosan salt or chitosan derivative may have an endotoxin concentration of less than 30 EU/g, preferably less than 20 EU/g, more preferably less than 15 EU/g, even more preferably less than 10 EU/g, and most preferably less than 5 EU/g.

The low endotoxin chitosan salt of the present invention is suitable for use as a haemostat for stemming blood flow.

Thus, according to a further aspect of the present invention, there is provided a low endotoxin chitosan salt as described herein for use as a haemostat for stemming blood flow. The low endotoxin chitosan salt can be used as a haemostat for internal or external bleeding. For chitosan salts used in surgery for internal bleeding, endotoxin concentration of less than 5 EU/g is desired.

The low endotoxin chitosan salt of the present invention may be incorporated into a wound dressing for superficial non-life threatening bleeding or life threatening bleeding.

Thus, according to a further aspect of the present invention, there is provided a low endotoxin chitosan salt as described herein for use in a wound dressing for superficial non-life threatening bleeding or life threatening bleeding.

The low endotoxin chitosan salt of the present invention is suitable for use in the preparation of a haemostatic wound dressing for stemming blood flow. According to a further aspect of the present invention, there is provided a haemostatic wound dressing comprising a low endotoxin chitosan salt as described herein.

According to a still further aspect of the present invention, there is provided a haemostatic material comprising a low endotoxin chitosan salt as described herein.

The haemostatic material and/or chitosan salt may be in any suitable form, such as particulate, powder, granular, flake, fibrous, gel, foam, sheet, film or liquid form.

According to a still further aspect of the present invention, there is provided a method of stemming blood flow comprising the steps of: optionally cleaning a wound area where possible; applying to said wound area a haemostatic wound dressing comprising a low endotoxin chitosan salt as described herein; and applying constant pressure to the wound area until a gel clot forms.

Constant pressure is preferably applied to the wound area for about three minutes or more.

Beneficially, the lower the concentration of alkali solution used in the preparation of the haemostatic material of the present invention, the better the material performs in penetrability, blood clotting and haemostasis.

BRIEF DESCRIPTION OF THE DRAWINGS

Embodiments of the present invention will now be described further in the following non-limiting examples with reference to the accompanying drawing in which:

FIG. 1 is a graph displaying the effect of different concentrations of acid salt by-product on the viscosity of a chitosan product in the different media.

DETAILED DESCRIPTION

Endotoxin Testing
1. Make up USP (United States Pharmacopia) extraction solution as detailed in USP for chitosan endotoxin testing (4.6 ml of 1M HCl and 45.4 ml endotoxin free water);
2. Extract by adding 0.1 g of the test chitosan product to 9.9 ml of USP extraction solution and leave for 48 hours at 37° C.;
3. After 48 hours, dilute 100 µl of the extract in 0.9 ml of endotoxin free water; and
4. Mix 100 µl of the above in 100 µl of Endotoxin Specific (ES) buffer provided by Charles River.

The resulting extract is tested using an Endosafe®-PTS™ handheld spectrophotometer that utilises FDA-licensed disposable cartridges. The extract process uses a 2000× dilution and a minimum test limit detection of 10 EU/g.

EXAMPLES

Example 1

50 g of chitosan was mixed with 50 g 1M NaOH for 10 mins. The resulting wet alkali chitosan crumb was dried immediately in a fluid bed drier at 40° C.
Initial Endotoxin of raw chitosan: 64.8 EU/g
Dry treated alkali Chitosan: <5 EU/g

Example 2

50 g of chitosan was mixed with 50 g 0.1M NaOH for 10 mins. The resulting wet alkali chitosan crumb was dried immediately in a fluid bed drier at 40° C.
Initial Endotoxin of raw chitosan: 64.8 EU/g
Dry treated alkali Chitosan: 16.3 EU/g

Example 3

50 g of chitosan was mixed with 50 g 0.05M NaOH for 10 mins. The resulting wet alkali chitosan crumb was dried immediately in a fluid bed drier at 40° C.
Initial Endotoxin of raw chitosan: 64.8 EU/g
Dry treated alkali Chitosan: 20.0 EU/g

Example 4

50 g of chitosan was mixed with 50 g 0.01M NaOH for 10 mins. The resulting wet alkali chitosan crumb was dried immediately in a fluid bed drier at 40° C.
Initial Endotoxin of raw chitosan: 64.8 EU/g
Dry treated alkali Chitosan: <30 EU/g The process can be scaled up and used to make larger batch sizes.

The process can be used on chitosan in different physical forms such as a chitosan fibre or chitosan fabric.

The process can also utilise a different base to sodium hydroxide, such as potassium hydroxide for example.

Examples 1-4 relate to the production of low endotoxin alkali chitosan. This low endotoxin alkali chitosan can subsequently be used as a raw material to make other chitosan based products. For example alkali chitosan can be neutralised to pH 7 to form a neutral chitosan by adding a low level of an appropriate acid that would react with the base to make a biocompatible salt. For example, if sodium hydroxide is used in the basic solution, it can be neutralised by the addition of hydrochloric acid. The product would contain a low amount of residual sodium chloride.

The low endotoxin alkali chitosan formed in Examples 1-4 can also be used to make a low endotoxin water soluble chitosan salt or other chitosan derivatives. Beneficially, this can be achieved without the need for a sterile environment, without the use of large quantities of expensive endotoxin free water and without the need for rinsing or washing. For example, a low endotoxin alkali chitosan can be reacted with a greater level of an appropriate acid. A small portion of the acid will react with the base to make a biocompatible salt.

In another example, low endotoxin alkali chitosan can also be used as a raw material for the manufacture of low endotoxin chitosan derivatives, such as carboxy methyl chitosan.

Effect of Acid Salt on Viscosity

Reacting the low endotoxin alkali chitosan with acid, to produce either a neutral pH chitosan or a chitosan salt, produces an acid salt by-product. The presence of this by-product can affect the performance of the chitosan product. For example, the level of by-product can affect the viscosity of a chitosan product in saline.

Referring to FIG. 1, there is shown the results of adding sodium lactate to saline in different concentrations, and the resulting effect of this on the viscosity of a 2 g sample of the current market-available chitosan product, CELOX®, in a 20 g solution of the different media after three minutes.

The base media was saline from body fluids, to which different levels of sodium lactate were added. The sodium lactate represented the by-product of the reaction between sodium hydroxide and lactic acid.

The results are set out in Table 1 and FIG. 1.

TABLE 1

| Concentration | Viscosity | | | |
|---|---|---|---|---|
| | Test 1 | Test 2 | Test 3 | Average |
| Saline | 55000 | 62000 | 59000 | 58667 |
| 1.5% | 54000 | 52000 | 61000 | 55667 |
| 2.5% | 50000 | 43000 | 39000 | 44000 |
| 5.0% | 35000 | 51000 | 31000 | 39000 |
| 7.5% | 35000 | 34000 | 38000 | 35667 |
| 10.0% | 37000 | 32000 | 36000 | 35000 |

It is clear from FIG. 1 that as the added salt level increases, the viscosity of the CELOX® in the media drops. It is therefore beneficial for there to be only a low level of residual salt by-product resulting in the chitosan products of the present invention.

Effect of Low Concentration Alkali Solution on Viscosity

The low endotoxin alkali chitosan of the present invention can be tested to demonstrate the effect of the treatment with acid on the viscosity of the chitosan polymer, considered to be a measure of molecular weight. The test comprises the following method steps:
a) weigh out 5 g of low endotoxin alkali chitosan granules;
b) weigh out 4.95 g of acetic acid in 600 ml beaker;
c) add 490.05 g deionised water to the beaker to make up 495 g of a 1% solution of acetic acid;
d) place the beaker on stirrer plate and turn on stir (increase as the viscosity of the solution increases;
e) add the chitosan granules to the acetic acid solution;
f) check the solution regularly until all the granules have dissolved and increase stirring level as the viscosity of the solution increases, if required;
g) leave the solution for a total of 24 hours, measured from the time the chitosan granules were introduced into the acetic acid solution;
h) attach a spindle 64 to a Brookfield Viscometer
i) set the spindle to 10 rpm;
j) insert the spindle into the solution to the mark on the spindle and turn the viscometer on and allow to stabilise;
k) record the viscosity (cPs) at selected time intervals.

Effect of Lowering the Concentration Alkali Solution

The effect of using a lower concentration of alkali solution in the process of the present invention can be tested in three experiments, focussing on (1) the percentage penetrability of saline into a test sample; (2) the time period to blood clotting; and (3) the percentage haemostasis in epigastric sever in-vivo models.

The general test method for (1) the percentage penetrability into saline is as follows: 5 mls of distilled water is added to a test tube. A drop of red food dye is added to the water. 3 g of sample haemostatic powder is gently tipped on top of the water such that a layer is formed. After 1 minute, the distance travelled by the water into the haemostatic powder is measured and recorded as percentage penetration.

The general test method for (2) the time period to blood clotting is as follows: 0.75 g of sample haemostatic powder is added to a test tube, to which 5 ml of heparinised rabbit blood is added. The test tube is then inverted and the time taken to fully clot the blood into a gel mass recorded.

The general test method for (3) the percentage haemostasis in epigastric sever in-vivo models is as follows: a 3-5 cm sever is made in the epigastric artery of a swine model (non-heparinised). The haemostatic material in granular form is applied and a 1 minute compression applied. If re-bleeding occurs, a further 1 minute compression is undertaken.

It is of course to be understood that the present invention is not intended to be restricted to the foregoing examples which are described by way of example only.

The invention claimed is:

1. A process for producing a low endotoxin alkali chitosan, chitin or a derivative thereof, the process comprising the steps of:
   (a) contacting chitosan, chitin, a chitosan derivative or a chitin derivative with an alkali solution having a concentration of from 0.01 M to 0.2 M to form a mixture, wherein the chitosan derivative or chitin derivative is selected from the group consisting of carboxymethyl chitosan, hydroxyl butyl chitin, N-acyl chitosan, O-acyl chitosan, N-alkyl chitosan, O-alkyl chitosan, N-alkylidene chitosan, O-sulfonyl chitosan, sulfated chitosan, phosphorylated chitosan, nitrated chitosan, alkalichitin, alkalichitosan, and metal chelates with chitosan; and
   (b) leaving the mixture for a period of less than 1 hour; and then
   (c) drying the mixture.

2. The process as claimed in claim 1, wherein the concentration of the alkali solution is about 0.1M.

3. The process as claimed in claim 1, wherein the alkali solution comprises an alkali or alkaline earth component selected from the following, either alone or in combination: metal hydroxides, metal carbonates, metal bisulphites, metal persilicates, conjugate bases and ammonium hydroxide, wherein the metal is optionally selected from sodium, potassium, calcium, or magnesium and wherein the alkali component is optionally selected from sodium hydroxide, potassium hydroxide or sodium carbonate.

4. The process as claimed in claim 1, wherein the alkali solution is sprayed onto the chitosan, chitin, a chitosan derivative or a chitin derivative or the chitosan, chitin, a chitosan derivative or a chitin derivative is mixed with the alkali solution.

5. The process as claimed in claim 1, wherein the mixture is left for a period of less than three minutes.

6. A process for producing a low endotoxin alkali chitosan, chitin or a derivative thereof, the process comprising the steps of:
   a. contacting chitosan, chitin, a chitosan derivative or a chitin derivative with an alkali solution having a concentration of from 0.01M to 0.2M to form a mixture, wherein the chitosan derivative or chitin derivative is selected from the group consisting of carboxymethyl chitosan, hydroxyl butyl chitin, N-acyl chitosan, O-acyl chitosan, N-alkyl chitosan O-alkyl chitosan, N-alkylidene chitosan, O-sulfonyl chitosan, sulfated chitosan, phosphorylated chitosan, nitrated chitosan, alkalichitin, alkalichitosan, and metal chelates with chitosan; and
   b. immediately drying the mixture.

7. The process as claimed in claim 1, wherein a preservative is added to the mixture of step (a), wherein the preservative is optionally selected from silver ions, zinc ions, chlorohexadine, or combinations thereof.

8. The process for producing a low endotoxin neutral chitosan, a chitosan salt or a chitosan derivative comprising the step of contacting an alkali chitosan prepared by the process of claim 1 with an acid.

9. The process as claimed in claim 8, wherein the step of contacting the alkali chitosan with an acid is performed before the drying step (c); wherein the acid is optionally sprayed onto the alkali chitosan or the alkali chitosan is mixed with the acid.

10. The process as claimed in claim 8, wherein the acid is selected from the following, either alone or in combination: organic acids optionally selected from the following, either alone or in combination: acetic acid, tartaric acid, citric acid, ascorbic acid, acetylsalicylic acid, gluconic acid and lactic acid; carboxylic acids; fatty acids optionally selected from the following, either alone or in combination: myristoleic acid, palmitoleic acid, sapienic acid, oleic acid, elaidic acid, vaccenic acid, linoleic acid, linoelaidic acid, α-Linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid; amino acids optionally selected from the following, either alone or in combination: histidine, lysine, aspartic acid, glutamic acid, glutamine, glycine, proline, taurine; lewis acids; monoprotic acids, diprotic acids, and mineral acids; polyprotic acids; and nucleic acids.

11. The process as claimed in claim 8, wherein the acid has a concentration of about 1M.

12. The process as claimed in claim 8, wherein the acid is present as an acid liquor comprising the acid and a non-solvent optionally selected from ethyl lactate, ethyl acetate, methyl acetate, ethanol, acetone, 80:20 mixture of ethanol: water or mixtures thereof.

13. The process as claimed in claim 12, wherein the ratio of chitosan to acid liquor is from about 5:1 to about 1:5.

14. The process as claimed in claim 8, further comprising the step of drying the reaction product.

15. The process as claimed in claim 12, wherein the alkali chitosan is mixed with the acid for about 5 minutes.

16. The process of claim 10, wherein the mineral acid is selected from the group consisting of hydrochloric acid, sulphuric acid, nitric acid, and combinations thereof.

17. The process of claim 1, wherein neither step of the process involves the use of endotoxin-free equipment.

18. The process of claim 1, wherein the quantity of chitosan, chitin, chitosan derivative or chitin derivative to alkali solution is from 1:10 to 10:1.

19. The process of claim 1, whereby the viscosity of the low endotoxin alkali chitosan, chitin, or derivative thereof is reduced by less than 25%.

20. The process of claim 1, wherein neither step of the process involves the use of a surfactant or phase transfer agents.

* * * * *